United States Patent [19]

Carter et al.

[11] Patent Number: 4,962,038

[45] Date of Patent: * Oct. 9, 1990

[54] MULTI-PURPOSE BLOOD DILUENT AND LYSING AGENT FOR DIFFERENTIAL DETERMINATION OF LYMPHOID-MYELOID POPULATION OF LEUKOCYTES

[75] Inventors: James H. Carter, Ft. Lauderdale; Stephen L. Ledis, Hialeah; Harold R. Crews, Miami, all of Fla.

[73] Assignee: Coulter Electronics, Inc., Hialeah, Fla.

[*] Notice: The portion of the term of this patent subsequent to Sep. 1, 1998 has been disclaimed.

[21] Appl. No.: 735,245

[22] Filed: May 17, 1985

Related U.S. Application Data

[63] Continuation of Ser. No. 395,530, Jul. 6, 1982, Pat. No. 4,521,518, which is a continuation of Ser. No. 159,782, Jun. 16, 1980, Pat. No. 4,346,018.

[51] Int. Cl.$^5$ .............................................. G01N 31/00
[52] U.S. Cl. .......................................... 436/10; 436/8; 436/17; 436/18; 252/408.1
[58] Field of Search ...................................... 436/8–18; 252/408; 424/2

[56] References Cited

U.S. PATENT DOCUMENTS

| | | | |
|---|---|---|---|
| 2,745,826 | 5/1956 | Semenoff et al. | 436/17 |
| 3,281,366 | 10/1966 | Judge et al. | 436/17 |
| 3,874,852 | 4/1975 | Hamill | 436/17 |
| 3,962,125 | 6/1976 | Armstrong | 436/10 |
| 4,102,810 | 7/1978 | Armstrong | 436/10 |
| 4,116,635 | 9/1978 | Jaegar | 436/17 |
| 4,185,964 | 1/1980 | Lancaster | 436/17 |
| 4,213,876 | 7/1980 | Crews et al. | 436/10 |
| 4,219,440 | 8/1980 | Runck et al. | 436/10 |
| 4,248,634 | 2/1981 | Forester | 436/17 |
| 4,286,963 | 9/1981 | Ledis et al. | 436/17 |
| 4,346,018 | 8/1981 | Carter et al. | 436/17 |
| 4,485,175 | 11/1984 | Ledis et al. | 436/17 |
| 4,528,274 | 7/1985 | Carter et al. | 436/17 |
| 4,529,705 | 7/1985 | Larsen | 436/17 |
| 4,617,275 | 10/1986 | Matsuda et al. | 436/10 |

OTHER PUBLICATIONS

Nicol, D. H. et al., J. Clin. Path. (1971) 24, p. 882.
Davis, R. E. et al., J. Jed. Lab. Technol. (1969) 26, pp. 26–30.
Barnard, D. E. et al., J. Clin. Path., 22, Suppl. Coll. Path. (1969) 3, pp. 26–30
Ballard, B. C. D., J. Clin. Path., 25, p. 460 (1972).
Hatch et al., Am. J. Clin. Path., 36, pp. 220–223 (1961).
Armak Arquad C-50 Bulletin.
J. M. England et al., Lancet, Mar. 1, 1975, p. 492.
J. M. England et al., Lancet, May 22, 1976, p. 1143.
J. M. England et al., J. Clin. Path., 27, p. 623 (1974).
P. A. Wycherly and M. J. O'Shea, J. Clin. Path., 31, p. 271 (1978).
D'Angelo et al., J. Clin. Path., 38, No. 6, pp. 658–662.
W. E. Love, J. Cell. and Comp. Physiol., 44, pp. 291–313 (1954).
"Hackh's Chemical Dictionary", McGraw Hill, Grant, 3rd Edition, p. 707.
"Chemistry of Organic Compounds", Sanders, Noller, 2nd Edition, 1957, pp. 241 and 243.

*Primary Examiner*—Robert A. Wax
*Assistant Examiner*—T. J. Wallen
*Attorney, Agent, or Firm*—Meredith P. Sparks; Gerald R. Hibnick

[57] ABSTRACT

An isotonic multipurpose blood diluent, and a method for use of this diluent with a weak lysing reagent system which is especially suitable for routine enumeration of traditional hemogram values, and also the determination of lymphoid-myeloid populations of leukocytes, particularly in automatic particle counting systems.

This blood diluent is capable of affording accurate, reproducible test results. It is an osmotically balanced aqueous solution of preselected pH containing Procaine hydrochloride for maintaining erythrocyte morphology during operation, N-(2-acetamido)iminodiacetic acid (ADA) as a blood cell stabilizing agent, and bacteriostatic agents including sodium 1-hydroxypyridine-2-thione, and dimethylolurea which, together with the ADA, allow preferential determination of myeloid-lymphoid leukocytes, and other hematological values.

The lysing agent is a mixture of an aqueous solution of at least one quaternary ammonium salt having surface active properties, and an alkali metal cyanide.

14 Claims, No Drawings

MULTI-PURPOSE BLOOD DILUENT AND LYSING AGENT FOR DIFFERENTIAL DETERMINATION OF LYMPHOID-MYELOID POPULATION OF LEUKOCYTES

This application is a continuation of application Ser. No. 06/395,530, filed Jul. 6, 1982 to issue.

BACKGROUND OF THE INVENTION invention concerns a blood diluent especially suitable for use in electronic enumeration and sizing of blood cells, determination of hemoglobin and their collective indices and platelet parameters in a single blood cell sample by means of suitable electronic instrumentation. The diluent comprises a stable water solution of chemical salts providing an electrolytic solution capable of conducting current to which a blood sample can be added so as to dilute the red blood cells, white blood cells, platelets and other blood components and enable the desired parameters of these blood components to be measured, counted and evaluated.

It is a common medical diagnostic procedure to analyze and test a blood sample of a patient in order to make certain classic determinations with respect to the blood sample. This procedure is an important tool for the physician. Six characteristically important parameters are referred to as red blood cell count (RBC), the hematocrit (HCT), the hemoglobin (HGB), the mean corpuscular volume (MCV), the mean corpuscular hemoglobin (MCH), and the mean corpuscular hemoglobin concentration (MCHC). A seventh important determination is white blood cell count (WBC).

Much effort has been devoted to the development of satisfactorily automated leukocyte differential systems. However, a need exists for reagent systems which will be easily adaptable to automatic blood counting instruments. In particular, it is desirable to develop reagents and methods for use with the Coulter Counter ® Model S Plus automated blood counter, manufactured by Coulter Electronics, Inc. of Hialeah, Fla., which will enable the cell volume data accumulated on a Coulter Channelyzer ® to discriminate two populations of leukocytes: (1) a lymphoid (lymphocytes) population, and (2) a myeloid (neutrophils, monocytes, eosinophils, and basophils) population. Such data are useful as a screening tool for spotting abnormal leukocyte ratios. Abnormal situations flagged out by this method give information of diagnostic significance, and for further study.

Separation of normal human leukocytes by volume distribution was first documented by Gauthier and colleagues, (Gauthier, J., Harel, P., Belanger, C. and Fraysse, J., Can. Med. Assoc. J. 97, 793, (1967) and Van Dilla and colleagues, (Van Dilla, M. A., Fulwyler, M. J. and Boone, I. U., Proc. Soc. Exp. Biol. Med. 125, 367, in 1967 as a possible clinical diagnostic method utilizing the principle of counting and sizing developed by Wallace H. Coulter and employed in Coulter Counter ® instruments. These methods were based on the fundamental property of all living cells to regulate their cell volume by genetic code information. Each type of cell in the circulating blood has its own characteristic volume ranging from as small as 3 cubic microns for platelets to 450 cubic microns for polymorphonuclear cells. Advanced Coulter Counter ® instruments have been designed to make use of this volume differential for the purposes of counting and determining the size distribution of platelets and erythrocytes to detect and monitor pathological states.

Electrical sizing of particles in suspension by a Coulter Counter ® type instrument has been previously described and documented by many clinical hematology investigators. It is well known that the form and size of the electrical pulse generated by a particle passing through a defined electrical field is influenced by several factors, including size, shape and conductance of the particles being counted. In blood cell preparations diluted in an isotonic salt solution, conductivity of the cell membrane is far lower than conductivity of the diluent, and therefore, blood cells may be considered to be electrically non-conducting for practical considerations.

Erythrocytes and the lymphoid leukocytes unfortunately overlap considerably in cell size, and it is not possible to count one in the presence of the other by size discrimination alone. Traditional practice involves the use of a strong lytic-surfactant reagent that stromatolyzes the erythrocytes, reducing them to very small particles or causing membrane solubilization, and strips the cytoplasm from both the lymphoid and the myeloid leukocytes, leaving only the lyse-resistant nuclei to be counted. Since original cell volume is drastically affected and reduced to a minimum, only a single population is visible by size distribution analysis. Experimental results indicate that shape changes in leukocytes are not as pronounced as shape changes in erythrocytes; action of a lytic agent reduces the leukocyte deformability even further.

The Coulter Counter ® Model S Plus automated blood cell counter is designed to dilute a sample of whole blood in an isotonic diluent, add a lysing agent, and then begin counting after 7.5 seconds. Data are collected for 4 seconds for erythrocytes and leukocytes and up to 20 seconds for platelets. Thus, a diluent-lysing system must provide erythrocyte lysing kinetics sufficiently rapid to effect complete stromatization during the lysing period, but not completely strip the leukocytes during this time. In addition, changes in leukocyte volume must be minimal during the data collection step, and ideally should be stable for several minutes. The reagent system must also preserve the integrity of the erythrocyte and platelet number and size distribution, the hemoglobin absorbance curve and the total leukocyte count. Finger stick bloods must be stable when pre-diluted in the isotonic diluent for at least two hours.

To achieve an analysis of the relative populations of lymphoid and myeloid cells in the blood, the leukocyte volume histogram must show cleanly separated lymphoid and myeloid peaks, with little erythrocyte debris, allowing valleys very close to the baseline. Integration of each peak will give the relative populations of the lymphoid and myeloid cells. The lymphoid peak has been demonstrated to contain lymphocytes and small atypical lymphocytes, while the myeloid peak contains polymorphonuclear cells, bands, monocytes, eosinophils, basophils and large atypical lymphocytes.

In U.S. Pat. No. 3,874,852 (1975) to Coulter Diagnostics, Inc., a formula is included for a composition containing quaternary ammonium salt detergent and cyanide to be employed as a lysing and chromagen-forming reagent for obtaining a single volume leukocyte count and hemoglobin determination in the Coulter Counter ® Model S. Further investigation was required to use quaternary ammonium salts as lysing agents for obtaining the two-population leukocyte count.

In copending patent application Ser. No. 096,697 filed 11/23/79, now U.S. Pat. No. 4,286,963 to Coulter Electronics, Inc. a lytic diluent for the rapid lysing of red blood cells in whole blood for making a differential determination of lymphoid/myeloid populations of leukocytes, and also measuring hemoglobin by chromagen formation, contains a mixture of an aqueous saline solution of at least one quaternary ammonium salt having surface acting properties, and certain additives such as 2-phenoxyethanol.

It is known that two volume distribution analysis is difficult because with many diluents, the two populations rapidly move into one. There is not enough time within which to make the computations for analysis.

SUMMARY OF THE INVENTION

The present invention relates to an isotonic multipurpose blood diluent, and a method for use of this diluent with a lysing reagent system to allow routine enumeration of traditional hemogram values, and also the display and calculation of the lymphoid/myeloid histogram of the leukocytes and their relative concentrations, particularly in automatic counting systems such as the automated Coulter Counter ® equipment with unmodified programming and an external or internal leukocyte Channelyzer ® instrument capability.

This multipurpose isotonic blood diluent comprises a cell stabilizing mixture of organic buffers, anesthetics, and germicides in an osmotically balanced and substantially neutral solution, and serves to slow the kinetics of cytoplasmic stripping from the leukocytes, while stabilizing the traditional hemogram parameters. More specifically, the isotonic diluent is an aqueous solution of:
1. N-(2-acetamido)iminodiacetic acid (ADA),
2. Procaine hydrochloride,
3. Chlorhexidene diacetate,
4. Dimethylolurea,
5. Sodium 1-hydroxypyridine-2-thione,
6. Sodium sulfate and sodium chloride the diluent being adjusted to a pH 7.0±0.1 with sodium hydroxide or hydrochloric acid solution, as necessary, and to an osmolality of 320±5 milliosmoles per kilogram with sodium chloride.

The lysing reagent is a mixture of an aqueous solution of at least one quaternary ammonium salt having surface active properties, and an alkali metal cyanide. Presentation of data may be accomplished using standard Coulter Counter ® equipment in conjunction with a Channelyzer ® and an X-Y plotter. Ancillary calculating and data handling devices are desirable for complete automation, but are not essential to performance of the measurements.

DETAILED DESCRIPTION OF THE INVENTION

Description of the Preferred Embodiments

The preferred formulation of the isotonic diluent is:

| Ingredient | Effective Concentration Range |
|---|---|
| Procaine hydrochloride | 0.11 g/L |
| N-(2-acetamido)iminodiacetic acid (ADA) | 1.40 g/L |
| Chlorhexidene diacetate | 0.02 g/L |
| Dimethylolurea | 1.00 g/L |
| Sodium 1-hydroxypyridine-2-thione | 0.50 g/L |
| Sodium hydroxide | 0.50 g/L |
| Sodium sulfate, anhydrous | 9.72 g/L |
| Sodium chloride | 4.50 g/L |

| Ingredient | Effective Concentration Range |
|---|---|
| Water | Sufficient for 1 liter |

This diluent is adjusted to pH 7.0±0.1 with sodium hydroxide or hydrochloric acid solution as necessary. The osmolality is adjusted to 320±5 milliosmoles per kilogram with sodium chloride.

The chemical and biological action of Procaine hydrochloride, sodium sulfate and sodium chloride is disclosed in U.S. patent application Ser. No. 936,570 filed 08/22/78, now U.S. Pat. No. 4,213,876. It is well known that blood cells contain ATPase enzymes that transport alkali metal cations associated with small anions (e.g. chloride) into and out of the cell by an energy-requiring mechanism in order to maintain osmotic balance, tergidity of the cell and proper membrane potentials. Sodium ions associated with the much larger sulfate anion are apparently not transported as readily due to greater differences in charge density between sulfate and chloride anions and the potential change in membrane charge when ions are transported into or out of the cell. Procaine hydrochloride, as one of a class of anesthetics, has been reported to have a stabilizing influence on the erythrocyte membrane, but the mode of action is uncertain. Seeman (P. Seeman, Biochemical Pharmacology 15, 1753, 1966) suggests that the hydrophobic portion of the Procaine molecule dissolves in the membrane, leaving the polar (charged) and near the outer surface, and causes expansion of the membrane as shown by electron microscopy. It is highly probable that this membrane expansion is due at least in part to changes in the membrane potential induced by the anesthetic and reinforced by salts of low ionic mobility. Balance of internal osmotic pressure within the cell is maintained by the inclusion of approximately 30 milliosmoles of sodium chloride. Sodium sulfate is also well known for its ability to solubilize abnormal plasma globulins and to reduce or eliminate turbidity in the hemoglobin solution due to elevated leukocyte counts.

The N-(2-acetamido)iminodiacetic acid (ADA) has previously been described as a ligand for metal cations (U.S. Pat. No. 4,116,635, Jaeger) and as an organic buffer. Its use in the present invention is predicated on its ability to assist weak quaternary ammonium salt lysing agents in reducing lysed erythrocyte debris to particle sizes electrically smaller than 45 cubic microns, thus preventing erythrocyte interference with the enumeration and distribution of leukocytes into two distinct populations (lymphoid and myeloid). In addition, ADA has been found to help stabilize the size distribution, cellular shape, and most importantly the high degree of cellular dispersion of erythrocytes and platelets to an extent not previously observed with other compounds. Although the mechanism of action of ADA has not been rigorously investigated, it is known to be a moderately strong ligand for group II alkali metals and group IIB transition metals, as well as a reasonably efficient buffer. Resembling an amino acid to a strong degree, ADA apparently is attracted to and interacts with the cell membrane proteins. It is then coordinated with metal cations giving the outer membrane surface a more positive charge "appearance" to the surrounding solution, thus encouraging solvation and anion attraction around the outer membrane. This coating of solvent molecules and anions effectively prevents approach and agglutination interaction with other cells in suspension. The buffering action of the ADA prevents changes in this "local" environment, precluding desolvation and loss of stability.

This mechanism, coupled with the action of Procaine and sodium sulfate, assists in the stabilization of the cellular components of the blood sample, rendering them essentially unchanged from their original state in the blood specimen in terms of number, size distribution and shape. This factor is of great diagnostic importance in the interpretation of the traditional hemogram parameters.

Chlorhexidene diacetate, though usually used as a virocide and germicide, is only marginally effective by itself at the concentration used, but significantly aids ADA in reducing the background debris that interferes with leukocyte size distribution enumeration. Chlorhexidene also bears some resemblance to the amines arginine and guanidine and might be expected to interact with membrane proteins by coordination and hydrogen bonding. As such, it apparently aids the lysing agents to stromatolyze completely the erythrocyte membranes.

Dimethylolurea, a condensate of formaldehyde and urea, is believed to react very slowly in solution at neutral pH with the leukocyte membranes to afford a measure of stability upon standing that is not evident upon removal of this compound. It is known as a bacteriostatic antiseptic compound, preventing growth of microorganisms at moderate concentrations. Other compounds which were joined to stabilize leukocytes are hexamethylenetetramine, and N-hydroxymethylacetamide.

Sodium 1-hydroxypyridine-2-thione (U.S. Pat. No. 2,745,826, Olin Matheson 1956) has been used as fungicide and bacteriocide in dandruff shampoos (U.S. Pat. Nos. 3,236,733 and 3,281,366, Procter and Gamble 1966) and is used here as a bacteriocide and fungicide that exhibits no apparent deleterious effect on the shape, size distribution or number of the cellular components in whole human blood.

The use of both dimethylolurea and sodium 1-hydroxypyridine-2-thione gives a very bacteriocidal product which is superior to that obtainable with either substance used alone. This combination gives a stable hemogram for both normal and abnormal samples while simultaneously allowing volume distribution information about white cells to be collected by an automated instrumentation system.

It is a primary aim of this diluent system to suitably stabilize cell size, shape and integrity of all blood cellular components to an extent not previously achieved in order to promote diagnostic accuracy of blood hemograms derived from automated volume distribution analysis and enumeration. The present invention allows the extension and improvement of prior arts by rendering the blood stream conditions of cells relatively unchanged when diluted and prepared for automated blood cell counting and sizing. When used in conjunction with an appropriate lysing agent, prior art may be extended to provide volume distribution information about leukocytes.

The described diluent will reproduce accurate hemograms with any semi-automated or automated Coulter ® blood cell counter, but will produce two volume leukocyte histograms only when used in conjunction with the lysing reagent of this invention.

The lysing agent is an aqueous solution of at least one quaternary ammonium salt having surface active properties, and an alkali metal cyanide, as described generally in U.S. Pat. No. 3,874,852 Coulter 1975. However, the effective range and concentration of ingredients stated herein must be followed in order to obtain satisfactory results by the method of this invention.

In the preferred compositions, the long chain alkyl in the following formula has 12-16 carbon atoms, the short chains are trimethyl, and $X^-$ is chloride or bromide.

The quaternary ammonium salt detergent has the formula:

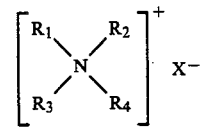

where $R_1$ is a long chain alkyl radical having 10 to 18 carbon atoms, $R_2$, $R_3$ and $R_4$ are short chain alkyl radicals having 1 to 6 carbon atoms, and $X^-$ is a salt forming radical such as Cl, Br, I, $PO_4$ and $CH_3SO_4$.

A preferred formulation for the lysing agent is:

| Ingredient | | Effective Concentration Range |
|---|---|---|
| Dodecyltrimethylammonium chloride 50% solution | 60 g/L | 40–70 g/L |
| Tetradecyltrimethylammonium bromide Mytab ® | 6 g/L | 4–7 g/L |
| Potassium cyanide | 300 mg/L | 250–500 mg/L |
| Water | sufficient for 1 Liter | |

The above lysing agent is very much weaker and slower in reaction rate than the currently used Lyse S ®II. Alternate quaternary ammonium salts that also are effective include Cetrimide ® (hexadecyltrimethylammonium bromide) and Bretol ® (cetyldimethylethylammonium bromide), both alone and in combination with dodecyltrimethylammonium chloride. The diluent system is apparently able to stabilize the leukocyte membrane sufficiently to slow the kinetics of the lysing agent reaction to a point where it is possible to distinguish the smaller volume of lymphoid cells from the larger volume of the myeloid series (neutrophils, monocytes, eosinophils and basophils). Repeated measurement of leukocyte size distribution have shown the histograms to be stable for up to 30 seconds before degeneration. Experimental results indicate that lymphoid cells are reduced essentially to their minimum cellular volume within the 7.5 second lysing time. The myeloid cells appear two to three times their terminal volume for up to 30 seconds after addition of the lysing agent after which the volume is slowly reduced until the myeloid fraction merges with the lymphoid fraction.

Using an erythrocyte calibrated Coulter ® Model S Plus and a calibrated Coulter ® Model C-1000 Channelyzer ® the volumes of the lymphoid and myeloid peaks after treatment with the reagent system were found to be in the vicinity of 85 cubic microns and 260 cubic microns, respectively, with narrow distribution widths. Leukocytes obtained from fresh whole blood by simple sedimentation on a Ficoll-Paque ® gradient were found to exhibit volumes of approximately 260 cubic microns for the lymphoid peak and 500 cubic microns for the myeloid peak with much wider distribution widths. A sample of fresh blood separated by centrifugation on a Ficoll-Paque ® gradient using a standard technique produced mononuclear cells (lymphocytes and monocytes) separated from granulocytes (neutrophils, eosinophils and basophils). The lymphocytes were found to be coincident with the lymphoid peak at 260 cubic microns while the monocytes were found to be centered around 550 cubic microns. The granulocyte fraction formed a rather broad peak centered around 500 cubic microns. The separation of the two populations was much more distinct with the chemically lysed blood from the Coulter Counter ® Model S Plus experiments than with the viable leukocytes obtained from the Ficoll-Paque ® method. It is, therefore, apparent that the lysing agent damages the leukocytes substantially, since their volumes are reduced two-to-three-fold in comparison to leukocytes obtained from the Ficoll-Paque ® separation of the same blood sample.

In the present invention incorporation of dodecyltrimethylammonium chloride has been found to reduce preferentially the volume of the lymphoid cells (i.e. a three-fold reduction in volume from 260 cubic microns to 85 cubic microns), while influencing the volume of the myeloid cells to a lesser extent (i.e. a two-fold reduction in volume from 500 cubic microns to 260 cubic microns. Dodecyltrimethylammonium chloride is actually a poor lysing agent itself. It appears to moderate the strong lytic effects of Mytab ®, slowing the lysing kinetics to a degree that allows measurement of the different cell nuclei volumes. The incorporation of dodecyltrimethylammonium bromide also gives a much cleaner, faster lysis of the erythrocytes and faster conversion of the hemoglobin with lower concentrations of Mytab ®, thus giving better stability to the leukocyte populations.

Preliminary data on more than one hundred normal and abnormal fresh blood specimens obtained from a blood donor center and local hospitals indicate a high degree of correlation between leukocyte population data from the Coulter Counter ® Model S Plus-Channelyzer ® system and manual 100 cell differentials. Although slight variation in myeloid and lymphoid fractions were observed, no drastic departures from correlation were noted.

Using the combination of the diluent and lysing reagent of the invention, spectrophotometric scans (wave length vs. absorbance) of the lysed blood from the leukocyte bath of the Coulter Counter ® Model S Plus produced hemoglobin curves essentially identical to those produced by Lyse S ®II; however, the absorbance at 540 mm and the resulting calculated hemoglobin values are approximately 0.2 g/L higher than with the combination of Isoton ®II and Lyse S ®II. Mean cell volume values have also been noted to be 1.0 to 1.5 cubic microns larger in the new two reagent system. All other parameters are virtually identical to those produced with the combination of Isoton ®II and Lyse S ®II.

We claim:

1. A lysing reagent for use with a diluted sample of whole blood, said lysing reagent comprising: a mixture of an aqueous solution formed by admixing at least two substantially pure quaternary ammonium salts, the combination of said salts being in an amount such that said reagent exhibits surface active properties effective to generate with automatic counting systems at least a two-volume leukocyte histogram, with separation of at least two leukocyte populations; one of said quaternary ammonium salts having the formula $I_a$ and the other of said quaternary salts having the formula $I_b$

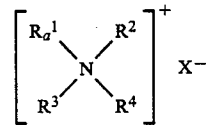

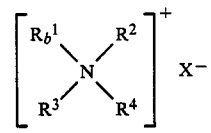

wherein $R_a^1$ and $R_b^1$ are long chain alkyl radicals; $R_a^1$ is long chain alkyl radical having 12 carbon atoms; $R_b^1$ is selected from the group consisting of long chain alkyl radicals having 14 carbon atoms, 16 carbon atoms, and mixtures thereof; $R^2$, $R^3$, and $R^4$ are short chain alkyl radicals having 1 to 6 carbon atoms; and $X^{31}$ is a salt forming radical, selected from the group consisting of $Cl^-$, $Br^-$, $I^-$, $PO_3^-$, $HSO_4^-$, and $CH_3SO_4^-$; and an isotonic blood diluent, said diluent comprising an aqueous solution of a blood cell stabilizing mixture including sodium sulfate and sodium chloride, said mixture being in suitable concentration to slow kinetics of cytoplasmic stripping from the leukocytes; such stripping being caused by said lysing reagent and being slowed to a degree which allows measurement of individual volumes of the cells of said leukocyte populations, while stabilizing hemogram parameters; and said diluent being substantially neutral.

2. A lysing reagent as defined in claim 1 wherein said diluent further includes sodium sulfate and sodium chloride.

3. A method for determining at least two populations of leukocytes in a sample of whole blood, said method comprising the steps of diluting said sample with isotonic diluent, and lysing said blood sample with a reagent which comprises a mixture of an aqueous solution formed by admixing at least two substantially pure quaternary ammonium salts, the combination of said salts being in an amount such that the combination exhibits surface active properties effective to stromatolyse erythrocytes and platelet cells to generate at least a two-volume leukocyte histogram, with separation of at least two leukocyte populations with automatic counting systems; one of said quaternary ammonium salts having the formula $I_a$ and the other of said quaternary salts having the formula $I_b$:
wherein $R_a^1$ and $R_b^1$ are long chain alkyl radicals; $R_a^1$ is long chain alkyl radical having 12 carbon atoms; $R_b^1$ is selected from the group consisting of long chain alkyl radicals having 14 carbon atoms, 16 carbon atoms, and mixtures thereof; $R^2$, $R^3$, and $R^4$ are short chain alkyl radicals having 1 to 6 carbon atoms; and $X^-$ is a salt forming radical, selected from the group consisting of $Cl^-$, $Br^-$, $I^-$, $PO_3^-$, $HSO_4^-$, and $CH_3SO_4^-$.

4. A method as claimed in claim 3 where $R_b$ is a long chain alkyl radical having 16 carbon atoms.

5. A method as claimed in claim 3 wherein $I_a$ and $I_b$, the short chains are trimethyl, and $X^-$ is selected from the group consisting of $Cl^-$ and $Br^-$.

6. A method as defined in claim 3 wherein the concentration of the ingredients is:

| | Ingredient | Effective Concentration Range |
|---|---|---|
| (a) | Dodecyltrimethylammonium chloride, 50% solution | 40 to 70 g/L |
| (b) | Tetradecyltrimethylammonium bromide | 4 to 7 g/L |
| (c) | Potassium cyanide | 250 to 500 mg/L |
| (d) | Water | Sufficient for 1 liter |

7. A method as defined in claim 3 having the following formulation:

| | Ingredient | Effective Concentration Range |
|---|---|---|
| (a) | Dodecyltrimethylammonium chloride, 50% solution | 60 g/L |
| (b) | Tetradecyltrimethylammonium bromide | 6 g/L |
| (c) | Potassium cyanide | 300 mg/L |
| (d) | Water | Sufficient for 1 liter |

8. A method as defined in claim 7 wherein said combination of quaternary ammonium salts exhibits surface active properties effective to slow the kinetics of the lysing to a degree that allows measurement of the individual cell volumes of said leukocyte populations.

9. A method as defined in claim 8 wherein said volumes of said leukocyte populations are stable from 7.5 to 30 seconds during data collection by the automatic counting system.

10. A method as defined in claim 3 wherein the blood is treated with an isotonic diluent comprising an aqueous solution of a blood cell stabilizing mixture, said mixture being in suitable concentration to slow the kinetics of cytoplasmic stripping from the leukocytes, while stabilizing the traditional hemogram parameters, and said diluent being substantially neutral.

11. A method as defined in claim 10 wherein said diluent further includes sodium sulfate and sodium chloride.

12. A method as defined in claim 11, wherein said blood stabilizing mixture comprises:
 (1) N-(2-acetamido)iminodiacetic acid,
 (2) Procaine hydrochloride,
 (3) at least one cell membrane stabilizer selected from the group consisting of:
  dimethylolurea,
  hexamethylenetetramine, and
  N-hydroxymethylacetamide, and
 (4) at least one germicide selected from the group consisting of:
  chlorhexidene diacetate,
  dimethylolurea, and
  sodium 1-hydroxypyridine-2-thione.

13. A method as defined in claim 12, wherein said cell membrane stabilizer is dimethylolurea and said germicide is dimethylolurea.

14. A lysing reagent for use with a diluted sample of whole blood, said lysing reagent comprising: a mixture of an aqueous solution formed by admixing at least two substantially pure quaternary ammonium salts, the combination of said salts being in an amount such that said reagent exhibits surface active properties effective to generate with automatic counting systems at least a two-volume leukocyte histogram, with separation of at least two leukocyte populations; one of said quaternary ammonium salts having the formula $I_a$ and the other of said quaternary salts having the formula $I_b$ wherein $R_a^1$ and $R_b^1$ are long chain alkyl radicals; $R_a^1$ is long chain alkyl radical having 12 carbon atoms; $R_b^1$ is selected from the group consisting of long chain alkyl radicals having 14 carbon atoms, 16 carbon atoms, and mixtures thereof; $R^2$, $R^3$, and $R^4$ are short chain alkyl radicals having 1 to 6 carbon atoms; and $X^{31}$ is a salt forming radical, selected from the group consisting of $Cl^-$, $Br^-$, $I^-$, $PO_3^-$, $HSO_4^-$, and $CH_3SO_4^-$; and an isotonic blood diluent, said diluent comprising an aqueous solution of a blood cell stabilizing mixture including sodium sulfate and sodium chloride, said mixture being in suitable concentration to slow kinetics of cytoplasmic stripping from the leukocytes; such stripping being caused by said lysing reagent and being slowed to a degree which allows measurement of individual volumes of the cells of said leukocyte populations, while stabilizing hemogram parameters; and said diluent being substantially neutral; said blood cell stabilizing mixture comprising:
 (1) N-(2-acetamido)iminodiacetic acid,
 (2) Procaine hydrochloride,
 (3) at least one cell membrane stabilizer selected from the group consisting of:
  dimethylolurea,
  hexamethylenetetramine, and
  N-hydroxymethylacetamide, and
 (4) at least one germicide selected from the group consisting of:
  chlorhexidene diacetate,
  dimethylolurea, and
  sodium 1-hydroxypyridine-2-thione.

* * * * *